(12) United States Patent
Röllinghoff et al.

(10) Patent No.: US 9,131,973 B2
(45) Date of Patent: Sep. 15, 2015

(54) OSTEOSYNTHESIS SYSTEM

(75) Inventors: Micha Röllinghoff, Olten (CH); Joanna Norström, Basel (CH); Marc Ammann, Niederhasli (CH)

(73) Assignee: Medartis AG, Basel (CH)

( * ) Notice: Subject to any disclaimer, the term of this patent is extended or adjusted under 35 U.S.C. 154(b) by 227 days.

(21) Appl. No.: 13/704,287

(22) PCT Filed: Jul. 9, 2010

(86) PCT No.: PCT/EP2010/059922
§ 371 (c)(1),
(2), (4) Date: Dec. 14, 2012

(87) PCT Pub. No.: WO2012/003884
PCT Pub. Date: Jan. 12, 2012

(65) Prior Publication Data
US 2013/0096629 A1    Apr. 18, 2013

(51) Int. Cl.
*A61B 17/88* (2006.01)
*A61B 17/80* (2006.01)
(Continued)

(52) U.S. Cl.
CPC ............... *A61B 17/88* (2013.01); *A61B 17/56* (2013.01); *A61B 17/58* (2013.01); *A61B 17/68* (2013.01); *A61B 17/80* (2013.01); *A61B 17/8004* (2013.01); *A61B 17/809* (2013.01); *A61B 17/8061* (2013.01); *A61B 17/746* (2013.01); *A61B 17/8052* (2013.01); *A61B 17/86* (2013.01)

(58) Field of Classification Search
CPC ........ A61B 17/56; A61B 17/58; A61B 17/68; A61B 17/746; A61B 17/80; A61B 17/8004; A61B 17/8052; A61B 17/8061; A61B 17/809; A61B 17/88

USPC ............. 606/70–71, 280–282, 286, 297
See application file for complete search history.

(56) References Cited

U.S. PATENT DOCUMENTS 7,001,388 B2 *   2/2006   Orbay et al. ............ 606/291
7,316,687 B2 *   1/2008   Aikins et al. ............ 606/70
(Continued)

FOREIGN PATENT DOCUMENTS

DE    37 22 852        1/1989
EP        0411273 A1 *  2/1991  ........... A61B 17/56
(Continued)

OTHER PUBLICATIONS

Translation for FR 2650500, Retrieved on Sep. 22, 2014 from <http://translationportal.epo.org/emtp/translate/?ACTION=description-retrieval&COUNTRY=FR&ENGINE=google&FORMAT=docdb&KIND=A1&LOCALE=en_EP&NUMBER=2650500&OPS=ops.epo.org/3.1&SRCLANG=fr&TRGLANG=en>.*

*Primary Examiner* — Larry E Waggle, Jr.
(74) *Attorney, Agent, or Firm* — Davis & Bujold, P.L.L.C.; Michael J. Bujold

(57) ABSTRACT

The present invention relates to an osteosynthesis system (1) comprising at least one bone plate (2), at least one blade (3) and at least one bone anchor (4). The blade (3) is configured such as to be insertable at a predefined angle (α) in relation to the bone plate (2) through a through hole (8) provided on a first longitudinal portion (6) of said bone plate (2) and into a bone. The blade (3) comprises at least one opening (9) which is configured such as to be aligned with at least one bone anchor hole (5) provided on a second part (7) of the bone plate (2) when the blade (3) is fully inserted into said through hole (8), such that the bone anchor (4) may be inserted through said bone anchor hole (5) and said opening (9).

19 Claims, 4 Drawing Sheets

(51) Int. Cl.
*A61B 17/58* (2006.01)
*A61B 17/68* (2006.01)
*A61B 17/56* (2006.01)
*A61B 17/74* (2006.01)
*A61B 17/86* (2006.01)

(56) References Cited

U.S. PATENT DOCUMENTS

| | | |
|---|---|---|
| 2003/0040748 A1 | 2/2003 | Aikins et al. |
| 2005/0143736 A1 | 6/2005 | Da Frota Carrera |
| 2005/0171544 A1 * | 8/2005 | Falkner, Jr. .................... 606/69 |
| 2006/0004361 A1 * | 1/2006 | Hayeck et al. ................ 606/69 |

FOREIGN PATENT DOCUMENTS

| | | | |
|---|---|---|---|
| FR | 2650500 | 2/1991 | |
| FR | 2650500 A1 * | 2/1991 | ............ A61B 17/58 |
| WO | 2005/044121 | 5/2005 | |
| WO | WO 2005044121 A1 * | 5/2005 | |
| WO | 2009/042783 | 4/2009 | |

* cited by examiner

OSTEOSYNTHESIS SYSTEM

FIELD OF THE INVENTION

This invention relates to a system for osteosynthesis and to a method for fracture fixation of a bone.

BACKGROUND OF THE INVENTION

Various systems for bone fracture fixation exist. Fractures of long bones may be treated by fixing an osteosynthesis plate on the bone bridging the fracture site. Alternatively, intramedular nails may be used.

Especially in the vicinity of a joint, such as shoulder, knee, elbow etc., high forces act on the bone. This is mainly caused by muscles and ligaments adhering to the bone in these areas. It is therefore especially important to provide fixation means which are strong enough to withstand the high forces and which offer good stability against distortion.

For fixation of fractures in the region of the proximal humerus there are various plate systems on the market. A few examples are the PHILOS plate (Synthes Inc., West Chester, Pa., USA), the AxSOS plate (Stryker Corp., Kalamazoo, Mich., USA) or the PERI-LOC proximal humerus locking plate (Smith & Nephew PLC., London, UK).

Fractures of the proximal humerus account for up to 4-5% of total fractures in humans. It is therefore a very frequent type of injury. As the muscles of the shoulder joint exert dragging forces on the fracture, dislocation of the fragments often occurs.

Further, there are many solutions directed to plates and osteosynthesis systems for fracture fixation on long bones in the area of joints. US 2003/0040748 describes a blade plate including a base portion and a blade portion. The blade portion is extending from the base portion at an angle and is inserted into the bone. A strut screw is insertable in a hole of the base portion such as to span the angle between the base and the blade portion.

Although this osteosynthesis system offers good stability against distortion of the plate, the insertion of the blade portion into the bone is complicated, since a cavity has to be reamed into the bone before the plate can be placed and secured by screws. Further, the strut screw spanning the fracture site does not offer stability against distortion, but rather serves to interlock and tension the blade and base portions. Also, due to the relatively bulky shape of the plate, this system may not be implanted with a minimal invasive surgery technique.

WO 2009/042783 describes a system for fracture fixation using a combination of an intramedullary nail and a small plate. Plate and nail are connected together through a spiral blade which is insertable through an opening in the plate into the bone and an opening of the nail.

DE 37 22 852 discloses a system comprising a first part in form of a plate to be positioned on the bone, a second part which may be inserted into bone as well as a truss screw which is insertable under an angle into the first plate part and which connects this part with the second part in the bone.

This system allows transforming bending forces, which may cause breakage of the plate, into dragging forces which are more readily absorbed by the components of the system. However, it does not provide for the prevention of distortion of the plate or the fracture.

SUMMARY OF THE INVENTION

The objective of the present invention therefore is to provide an osteosynthesis system avoiding the disadvantages known in the state of the art and specifically to provide for a system which provides good stability against bending and/or torsion forces and which may be implanted using a minimal invasive surgery technique. This objective is solved by a system as described below.

The system for osteosynthesis of bone fractures of the present invention comprises:
at least one bone plate, said bone plate having at least a first longitudinal plate portion with at least one through hole, and a second plate portion, with at least one bone anchor hole;
at least one blade with a longitudinal axis; and
at least one bone anchor.

The at least one blade further comprises at least one opening and is configured such as to be insertable at a predetermined angle smaller than 90° in relation to the bone plate through said through hole into a bone, such that the blade is generally pointing in the direction of the second part of the bone plate. The at least one opening is configured such as to be aligned with said at least one bone anchor hole when the blade is fully inserted into said through hole, such that the bone anchor may be inserted through said bone anchor hole and said opening.

The bone plate comprises an upper side and a lower side, which is intended to be placed onto a bone. The first portion of the bone plate has a longitudinal configuration, i.e. it is longer than wide. Such plate configurations are widely known in the art and are mainly used as plates on long bones. The longitudinal plate portion includes a central axis which is preferably in the form of a straight line. Alternatively, the central axis may also be curved, in the form of a sine wave or of any other suitable configuration. The first longitudinal plate portion further includes two edges arranged on either side of the central axis. These edges preferably are parallel to the central axis. Alternatively, the edges may also be curved or inclined towards or away of the central axis. Preferably, both edges are parallel to each other and/or symmetrically arranged about the central axis. The first longitudinal portion of the bone plate further comprises at least one through hole, i.e. an opening of defined shape spanning from the upper face to the lower face.

The second portion of the plate may also be of longitudinal shape. Preferably, the second portion of the plate has another shape, such as round, oval, polygonal or any other suitable shape. The second portion of the bone plate comprises at least one bone anchor hole. The bone anchor hole is adapted for the insertion of a suitable bone anchor.

Preferably, both the first longitudinal portion and the second portion of the bone plate are integral with each other. Alternatively, both portions may be separate and joined together before or during implantation by any suitable means, such as gluing, welding, soldering, screwing, by means of a form-fit connection or the like. Further alternatively, both portions may be attached to one another by means of at least one intermediate portion. However, it is important that both portions are strongly connected with each other after implantation. Most preferably, both portions are integrally formed out of the same piece of material.

The bone plate preferably comprises or is made of a biocompatible material. More preferably, the bone plate comprises or is made of a metallic material such as titanium, a titanium alloy, such as TAN or TAV, a cobalt chromium alloy, a magnesium alloy, a nickel titanium alloy and/or steel. Alternatively and depending on the intended indication for the bone plate, the bone plate may also comprise or be made of a biocompatible polymer material, such as PEEK. Alternatively, the bone plate may comprise or be made of a biodegradable material, such as a resorbable magnesium alloy or a resorbable polymer material.

The system further also comprises a blade. A "Blade" as understood herein means a structure which is insertable into bone and which is shaped and dimensioned such as to secure a fracture against bending and torsion forces. Hence, a blade has a structure with a non-circular cross section. Preferably the cross-section of the blade is rectangular, triangular, oval or polygonal. Most preferably, the blade is helically twisted.

The blade of the present invention comprises a longitudinal axis and at least one opening. The blade is insertable at a fixed angle in relation to the bone plate into the at least one through hole of the first longitudinal plate portion. The angle between the longitudinal axis of the blade and the lower side of the plate is thereby less than 90° and selected such that the blade is oriented in the direction of the second portion of the bone plate. Preferably, the angle is thereby from 30° to 60°. For the system to provide good stabilization of the fracture, the angle between the longitudinal axis of the blade and the lower side of the plate as well as the length of the blade are selected such that the blade is insertable through the fracture zone. Further, the at least one opening provided in the blade is located such that it is aligned with the at least one bone anchor hole of the second portion of the bone plate. This allows driving a bone anchor through both the bone anchor hole as well as the opening in the blade, thus forming a truss-like structure between the bone plate, the bone anchor and the blade.

The opening of the blade may include a thread matching a thread of the bone anchor. Preferably, the opening does not include a tread. This almost eliminates the formation of wear debris in the bone. The opening is further dimensioned such as to approximately match the diameter of the at least one bone anchor, at least along one cross-sectional plane of said opening.

Such a configuration stabilizes the fracture against distortion and/or tilting. Further, the truss-like structure allows better distribution of forces acting on the system, especially bending forces on the bone plate. This reduces the risk of secondary loss of reduction and breakage or deformation of the bone plate. Further, this configuration provides a large supporting surface and allows the distribution of forces on multiple structures.

Suitable bone anchors for the ostesynthesis system according to the present invention are pins, pegs, screws or the like. Preferably, the bone anchors are configured such as to provide good monocortical, bicortical and/or cancellous fixation in bone.

The blade preferably further comprises connection means to be reversibly connected to the bone plate. Preferably, the blade and the plate are configured to be interconnected by means of at least one screw, pin or peg. Further, the blade preferably additionally comprises a connecting element adapted to be inserted into a mating recess provided in the at least one through hole of the bone plate. The connecting element preferably is in the form of a flange which may be fittingly inserted into the recess.

The blade comprises a first end, which is insertable into bone, and a second end which is preferably reversibly connectable to the bone plate. The blade preferably further includes at least one fin element extending on one lateral side of the longitudinal axis from the first end to the second end. Said fin element includes a lateral edge which is separated from the longitudinal axis of the blade by a distance D. Said distance D preferably is constant along the length of the blade. Alternatively said distance D may also increase from the first end towards the second end. Further, said fin element preferably winds around said longitudinal axis in a spiral manner. Such a spiral blade configuration allows insertion of the blade into the bone by a twisting motion. More preferably the blade includes two fin elements winding around the longitudinal axis in a spiral manner. A spiral blade with two fin elements provides for an increased stabilization of the fracture against axial bending and torsion.

Alternatively, the blade may include more fin elements, such as three or four fin elements, depending on the intended indication of the osteosynthesis system. Of course the at least one through hole of the first longitudinal portion of the bone plate has to be shaped and sized such as to be able to accommodate a blade with the appropriate number of fin elements.

The blade preferably comprises or is made of a biocompatible material, more preferably a metallic material such as titanium, a titanium alloy, like TAN or TAV, a cobalt chromium alloy, a magnesium alloy, a nickel titanium alloy and/or steel. Alternatively and depending on the intended indication, the blade may also comprise or be made of a biocompatible polymer material, such as PEEK. Alternatively, the blade comprises or is made of a biodegradable material, such as a resorbable magnesium alloy or a resorbable polymer material.

The bone plate and the blade may comprise or be made of the same material.

The longitudinal axis of the blade preferably is in the form of a straight line. Alternatively, the longitudinal axis may also be provided as a curved line with a constant radius of curvature. The curvature of the blade is thereby configured such that, when the blade is fully inserted, the angle between the longitudinal axis at the first end of the blade and the lower side of the bone plate is smaller than the insertion angle of the blade. In a preferred embodiment, the longitudinal axis at the first end of the blade is parallel to the underside of the plate when the blade is fully inserted.

Preferably, said at least one fin element winds around said longitudinal axis 0.25 turns of 360°, i.e. 90°. Having a winding of less than one turn allows for easy insertion and removal of the blade into the bone. Further, a twist of 0.25 turns, i.e. of 90° allows for insertion of a blade with one or two fins in the through hole of the second portion of the bone plate parallel to the longitudinal axis of the bone plate. By the turn of 90°, the first end of the blade will have fins generally transverse to the insertion direction of the at least one bone anchor, which allows for an optimal transfer of forces between the bone anchor and the blade. Alternatively, the at least one fin element winds around the longitudinal axis by a turn of 270° or 450°, i.e. 0.75 and 1.25 turns of 360°.

Further alternatively, the at least one fin element winds around the longitudinal axis of the blade for multiple turns. The fin element thereby winds around the longitudinal axis like a thread of a screw. However, it is important that the lateral edge of the at least one fin element is separated from the longitudinal axis by a distance D which is sufficiently large to allow the arrangement of an opening for a bone anchor on said fin element. Additionally, the distance D must be sufficiently large so that the at least one fin element allows for a good stabilization of the fracture especially against torsion movements. It is therefore preferable that in the case that the blade is configured with at least one thread-like fin element, the thread-like structure is provided with a large thread depth.

The blade preferably comprises one or more fin elements, most preferably arranged at an angle of 180°, 120° or 90° from one another, respectively. Such a symmetrical distribution of the fin elements provides for a strong anchorage of the blade within a bone and an even distribution of any forces acting on the blade. Alternatively, the fin elements may also be arranged asymmetrically to each other. For example, a blade with three fin elements may provide for two fin elements separated by an angle of 60° while their separation from the third fin element is 150°. Of course any suitable number of fin elements as well as angular distribution of the fins may be chosen.

Preferably said second portion of said bone plate and said blade comprise at least one additional bone anchor hole and at least one additional opening which are configured such as to be respectively aligned when the blade is fully inserted into the through hole of the first longitudinal portion of the bone plate. More preferably the second portion of the bone plate and the blade additionally comprise one or more additional bone anchor holes and additional openings, respectively. This allows formation of additional truss-like structures between the bone plate, the blade and a bone anchor, thus further stabilizing the fracture fixation.

The second portion of the bone plate preferably comprises at least one auxiliary bone anchor hole. This auxiliary bone anchor hole is arranged such that an auxiliary bone anchor may be inserted into the bone without contacting the blade. This may be achieved by having the central axis of the hole arranged such that it does not intercept the blade and/or by providing means to insert a bone anchor under variable angles. With these auxiliary bone anchors, the second portion of the bone plate may be better anchored to the bone or to additional fracture fragments.

Said at least one auxiliary bone anchor hole preferably further comprises a locking element to lock a corresponding outer contour of an auxiliary bone anchor, more preferably in the form of a locking contour. A locking element, especially in the form of a locking contour allows insertion and locking of the auxiliary bone anchors under various angles. A suitable exemplary locking contour is described in EP 1 608 278. This allows an optimal locking of the second portion of the bone plate on the bone or further allows fixation of further fracture fragments at a fixed angle.

Alternatively, said second portion of the bone plate comprises a head section bulging outwards in the plane of the bone plate. Such a configuration is especially suitable when the osteosynthesis system of the present invention is used in the vicinity of a joint on a long bone, as the second portion of the bone plate may be placed on and fixed to the epiphysis of said long bone.

Preferably, the second portion is sized and shaped such as to be placed on the proximal end of the humerus and the first longitudinal portion is adapted to be placed on the methaphysis of the humerus. Thus, said first and said second portions have dimensions and are curved in such a way as to fit the outer contour of the humerus. Alternatively, the portions may be sized and shaped in such a way as to be placed on either the proximal or distal end of any long bone, such as ulna, radius, femur, tibia or fibula. Further alternatively, both portions of the bone plate may be sized and shaped such as to be placed on any other bone, such as phalangeal bones or metacarpals of the hand.

The bone plate preferably further comprises suture holes arranged at least on the outer rim of said second portion. This allows for the fixation of sutures to the plate, e.g. to hold or fix tissue to the plate, such as tendons or ligaments.

Said first longitudinal portion of the bone plate preferably further comprises at least one bone auxiliary anchor hole, preferably including a locking element to lock an auxiliary bone anchor in said hole. This allows anchoring the first longitudinal portion of the bone plate onto a bone. These auxiliary bone anchor holes may be arranged spaced apart from one another along the longitudinal axis of the first portion. Alternatively, one or several auxiliary bone anchor holes on the first longitudinal part of the bone plate are arranged slightly spaced apart from and on either side of the central axis of said first longitudinal portion.

Preferably at least one of said bone anchor, additional bone anchor and/or auxiliary bone anchor is a bone screw, preferably a bone screw with a double thread. Use of bone screws allows for a good anchoring in the bone. "Double thread" as understood herein means a screw having two intertwined threads with the same thread pitch. Alternatively, said at least one bone anchor, additional bone anchor and/or auxiliary bone anchor is a peg and/or a pin.

The blade is preferably configured such as to be self drilling and self cutting. This means that the blade may be inserted into the bone without the need to drill or ream a blade insertion channel first. A self drilling and/or self cutting blade preferably comprises a drilling point at its first end and/or sharp edges on the fin elements.

Further, the osteosynthesis system of the present invention comprises a set with a multiplicity of blades having different predefined insertion angles and/or lengths. Preferably, the set comprises two, three, four, five or more blades with different angles and/or lengths. This allows the selection of a blade having an optimal predefined insertion angle and/or length by the surgeon.

Alternatively, the through hole and the blade may be configured such that the blade may be inserted and locked at varying angles, e.g. by a special locking contour.

A further object of the present invention is to provide for a method of treatment of a fractured bone. This problem is solved with a method according to claim 13.

The method for fracture fixation of a bone, in particular using a system according to the present invention, comprises the steps of:

Placing a bone plate on said fractured bone, wherein a first longitudinal portion of the plate is placed on a first bone fragment on one side of the fracture and a second portion of the bone plate is placed on at least a second bone fragment on the other side of the fracture;

Inserting a blade at an angle in relation to the bone plate through a through hole provided on the first portion of the bone plate into the bone, wherein said angle is selected such that the blade points in the direction of the second part of the bone plate;

Inserting a bone anchor into the bone through at least one bone anchor hole provided on the second portion of the bone plate and through said at least one opening of the blade.

This method allows a stable fixation of a fracture, which is well secured against axial bending and torsion forces or twisting forces.

The bone anchor is preferably inserted into the bone using a guide member. The guide member facilitates insertion of the bone anchor through the opening of the blade within the hole, as the insertion direction of the anchor is preset by the guide member. The guide member may provide further guiding for the insertion of additional bone anchors into the bone.

The method according to the present invention may alternatively also comprise the additional step of reaming a blade insertion channel, preferably using a chisel. This may facilitate the insertion of the blade. Further, this step may be necessary if the blade is not self-drilling and/or self cutting.

BRIEF DESCRIPTION OF THE DRAWINGS

Further details and embodiments of the present invention will become apparent from the following examples and figures.

DETAILED DESCRIPTION OF THE INVENTION

Figure 1:
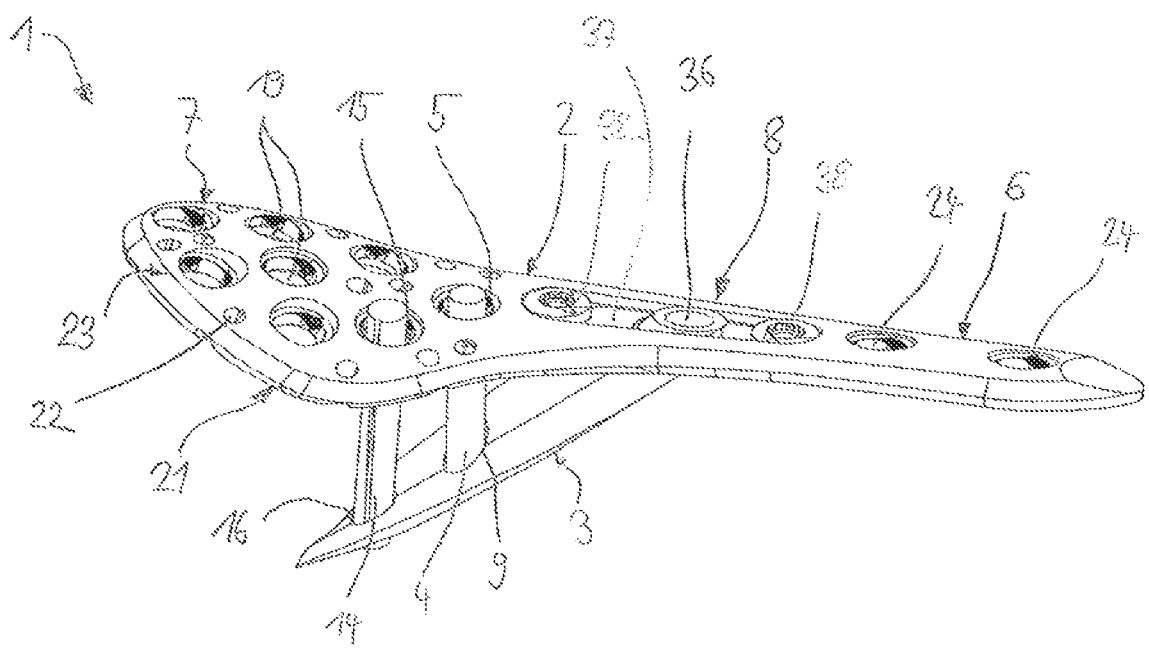
FIG. 1: Shows an exemplary embodiment of an osteosynthesis system according to the present invention.

FIG. 1 shows an exemplary embodiment of an osteosynthesis system 1 comprising a bone plate 2, a blade 3 as well a bone anchor 4. In this embodiment one additional bone anchor 14 is shown. Bone anchor 4 is inserted in bone anchor hole 5 and extends towards opening 9 in blade 3. Accordingly, additional bone anchor 14 is inserted into bone anchor hole 15 and extends towards additional opening 16 in blade 3. Blade 3 is fully inserted in through hole 8 and is attached to bone plate 2 by fixation means. In this embodiment the fixation means comprise two set screws 38 which may be screwed into two corresponding screw holes provided within recess 34. The set screws 38 are thereby holding a flange 37 of the blade 3. Additionally, the blade 3 comprises a handling adaptor 36, shown here as round opening which is configured such that handling means, e.g. a handle, may be used to insert blade 3. Alternatively other fixation means such as bolts, pins, a form-fit connection or any other suitable type of fixation may be used. Through hole 8 is located on a first longitudinal portion 6 of bone plate 2. This first portion 6 additionally comprises two auxiliary bone anchor holes 24, which preferably include locking means, such as a locking contour to lock a bone anchor having a matching locking contour. By insertion of auxiliary bone anchors in auxiliary bone anchor holes 24 the bone plate 2 may be fixed onto a first fragment of a bone. The bone plate 2 further comprises a second portion 7. In this embodiment the second portion 7 has a head section 21 bulging outwards sideways of the bone plate 2. The second portion 7 alternatively may be of any suitable shape depending on the indication of the bone plate 2. In this embodiment the second portion 7 further comprises auxiliary bone anchor holes 19, which preferably include locking means such as a locking contour to lock an auxiliary bone anchors including a matching locking contour. It is preferred that the auxiliary bone anchors may be locked into the auxiliary bone anchor holes 19 at various angles in relation to the bone plate 2. As may be seen on this figure, blade 3 is inserted into through hole 8 at a predefined and fixed angle in respect to bone plate 2. The angle is selected in such a way that blade 3 spans through the fracture of a bone. The predefined insertion angle of the blade 3 is specific for the blade 3 selected by the surgeon. Preferably the osteosynthesis system 1 includes a plurality of blades 3 with different predetermined insertion angles. Openings 9, 16 on blade 3 are arranged such that when the blade 3 is fully inserted in through hole 8 they are aligned with respective bone anchor holes 5, 15 on the second portion 7 of the bone plate 2. Once bone anchors 4, 14 are inserted, this leads to the formation of a truss-like structure between bone plate 2, blade 3 and bone anchors 4, 14.

Figure 2:
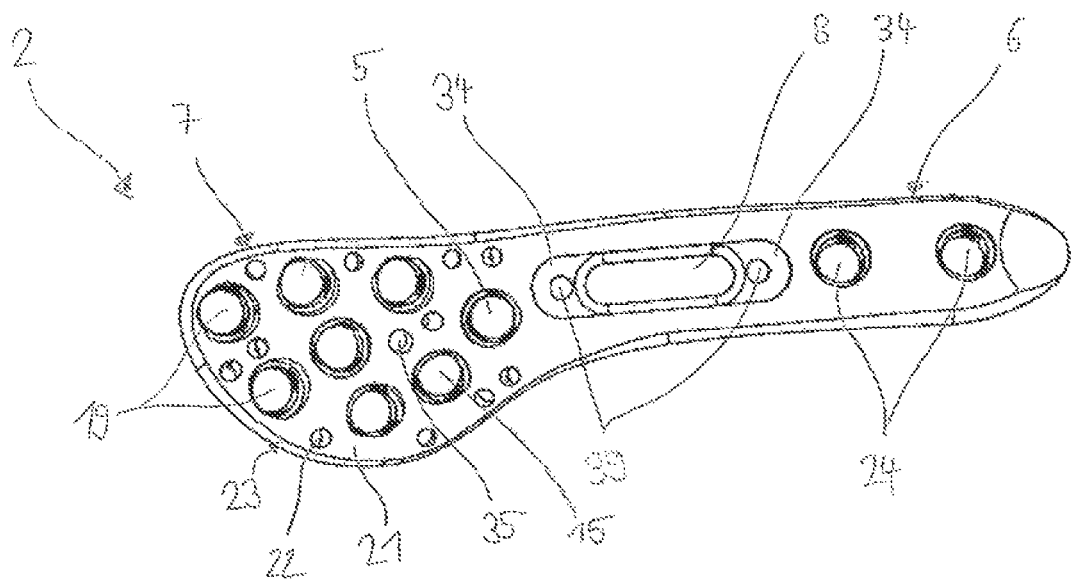
FIG. 2: is a representation of a bone plate from the embodiment shown in FIG. 1 viewed from the upper side.

FIG. 2 is a representation of a bone plate 2 of an osteosynthesis system 1 according to the present invention. The first longitudinal portion 6 of bone plate 2 comprises through hole 8 as well as two auxiliary bone anchor holes 24. Through hole 8 is provided in the form of a longitudinal slot. Additionally through hole 8 is flanked by a recess 34 configured such as to act as a counter sink for fixation means. In this embodiment the fixation means comprises two holes 39 within recess 34 as well as two set screws (not shown) intended to fix blade 3 to the bone plate 2. The second portion 7 of the bone plate 2 comprises a bone anchor hole 5 as well as additional bone anchor holes 15. These holes 5, 15 are configured such that their axes are aligned with openings 9, 16 of blade 3 when blade 3 is fully inserted within through hole 8. Further, second portion 7 comprises auxiliary bone anchor holes 19 as well as suture holes 22. The suture holes 22 are mainly located at the rim 23 of second portion 7. Additionally the second portion 7 includes attachment means 35 to attach a guide member onto the second portion 7.

Figures 3A, 3B, 3C:
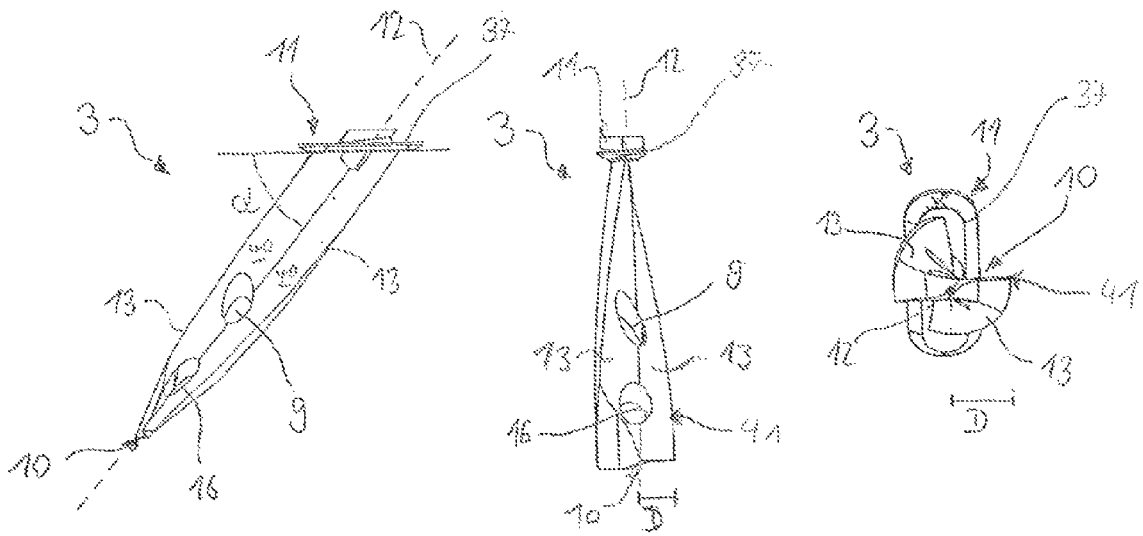
FIG. 3a-3c: are representations of a blade viewed from different sides.

FIG. 3 is a representation of the blade 3 of the osteosynthesis system 1 of FIG. 1. In FIG. 3a the blade 3 is shown in a side view. No bone plate is shown for visibility reasons. However, a lower side of a bone plate is exemplarily illustrated with a line. The blade 3 comprises a first end 10, which is intended to be inserted into bone, as well as a second end 11, which includes flange 37. Longitudinal axis 12 spans from the first end 10 to the second end 11. Two fin elements 13 additionally span from the first end 10 towards the second end 11. The fin elements 13 are configured such as to wind around the longitudinal axis 12 in a spiral manner. In this embodiment, fin elements 13 are wound around the longitudinal axis 12 0.25 turns of 360°. This equals a winding of 90° of the fin elements 13 around the longitudinal axis 12. This configuration allows for the fin elements 13 to have surfaces 40 oriented towards the bone plate 2 at the first end 10 of the blade 3 when the blade 3 is fully inserted into the through hole 8. This allows for an optimal alignment with the axis of the bone anchor holes 5, 15. Further, at the second end 11, fin elements 13 are oriented in the direction of the longitudinal axis of the first longitudinal portion 6 of the bone plate 2, thereby allowing arrangement of the through hole 8 as longitudinal hole along said axis. The longitudinal axis 12 of the blade 3 is angled relative to the plane of the first longitudinal portion 6 in the direction of the second portion 7 by an angle a. This angle a is selected such that the blade 3 may be inserted through hole 8 into a first fragment of a bone and further through the fracture into a second fragment of the bone. The angle a is less than 90° and selected such that the blade 3 points in the direction of the second portion 7. FIG. 3b shows the blade 3 along a plane through the longitudinal axis 12. This figure shows the winding of the fin elements 13 around the longitudinal axis 12. As may be seen, the surfaces 40 of the fins 13 are pointing towards the bone plate 3 at the first end 10. The fin element 13 has an edge 41 which is at a distance D from the longitudinal axis 12 of the blade 3. FIG. 3c shows the blade 3 from below along the longitudinal axis 12. Again on this figure the twist of the fin elements 13 around the longitudinal axis 12 as well as the distance D between the edge 41 and the longitudinal axis 12 of the fin element 13 may be seen.

Figure 4:
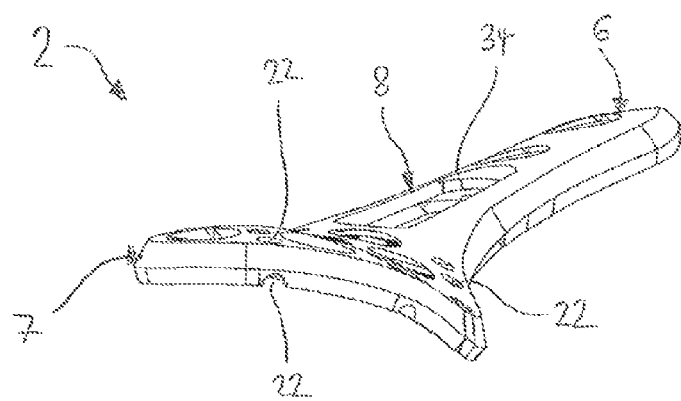
FIG. 4: shows the bone plate of FIG. 2 as viewed from the front of the second portion.

FIG. 4 is a representation of the bone plate 2 of FIG. 2 viewed along the second portion 7. As can be seen, the second portion 7 is bent such as to be placed on the epiphysis of a long bone. Preferably, the second portion 7 is sized and shaped such as to be placed on the proximal end of the humerus. Accordingly, the first longitudinal portion 6 of the bone plate 2 is sized and shaped such as to be placed on the metaphysis of along bone, again preferably on the metaphysis of the humerus. Suture holes 22 provide a connection between the upper face of the bone plate 2 to the rim 23 of the second portion 7. In order to be able to pass a suture through suture holes 22 the suture holes 22 provide for a recess on the lower face of the second part of the bone plate 2, thereby forming a channel between the bone and the lower face of the second portion 7.

Figure 5:
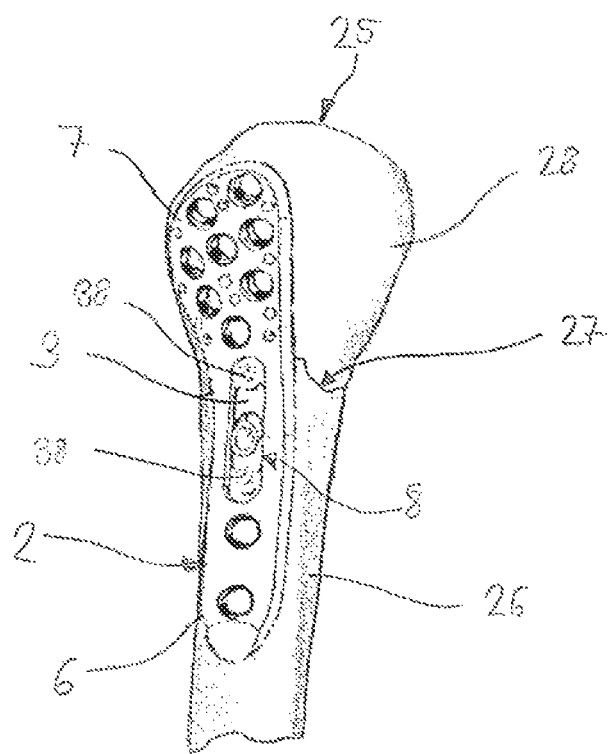
FIG. 5: shows the osteosynthesis system of FIG. 1 placed on a bone.
Figure 6A:
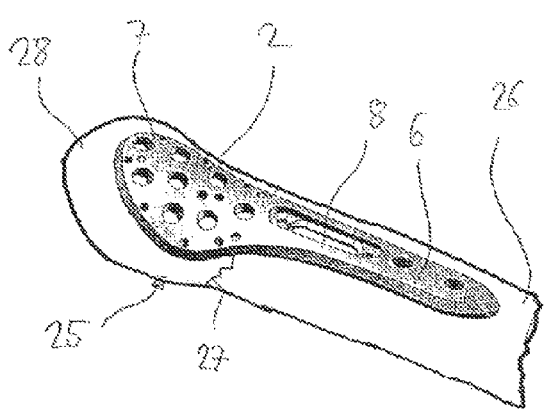
FIG. 6a-6e: represent a method for fixation of a bone fracture according to the present invention.
Figure 6B:
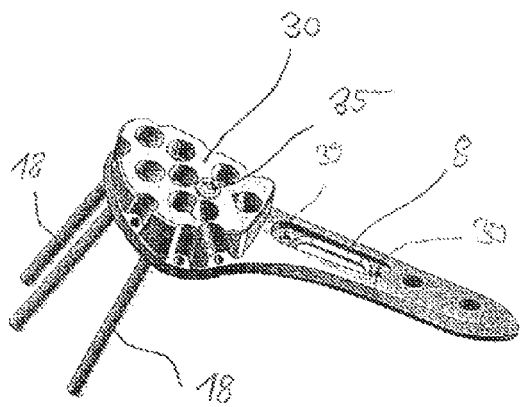
Figure 6C:
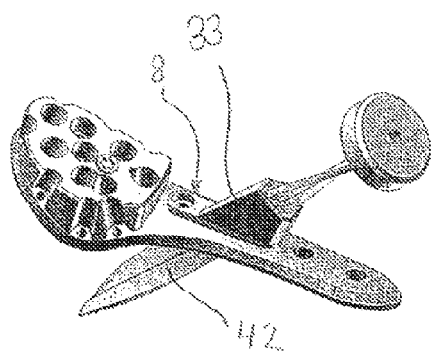
Figure 6D:
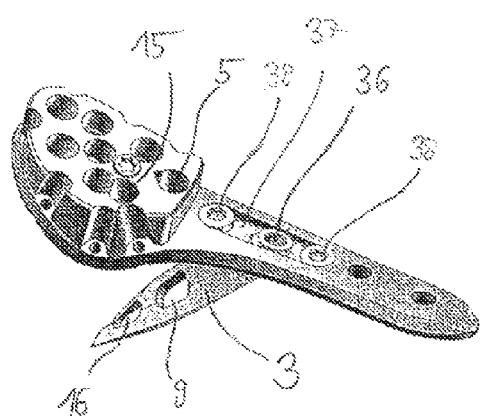
Figure 6E:
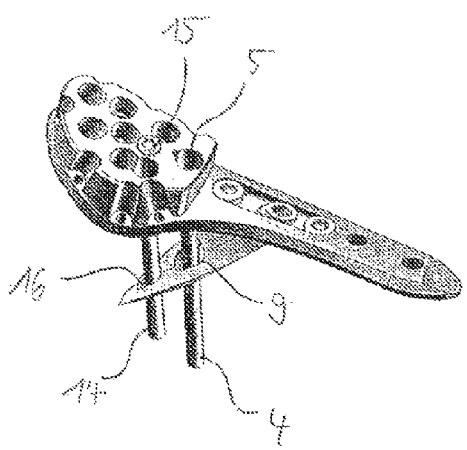

FIG. 5 is a representation of an osteosynthesis system 1 placed on a bone 25. The bone 25 has a fracture 26 which divides the bone 25 into a first fragment 26 and a second fragment 28. The bone plate 2 is placed on the bone 25 such that the first longitudinal portion 6 is on the first fragment 26 and the second portion 7 is on the second fragment 28. Further, placement of the plate 2 as well as the angle of blade 3 has to be selected such that blade 3 spans from the first fragment 26 through the fracture 27 into the second fragment 28. In this figure no bone anchors 4, 14 and no auxiliary bone anchors are shown. Only the blade 3, which is fully inserted into through hole 8, is shown. The blade 3 is attached to the bone plate 2 by means of the fixation means which are depicted as two set screws 38.

FIG. 6 shows a method for fracture fixation according to the present invention, preferably using an osteosynthesis system 1 as described herein. FIG. 6a shows a first step of the method. In this step the bone plate 2 is placed on a bone 25. The bone 25 has a fracture 27 which separates the bone 25 into a first fragment 26 and a second fragment 28. The bone plate 2 is placed on the bone 25 such that the first longitudinal portion 6 is on the first fragment 26 and the second portion 7 is on the second fragment 28. The next step is shown in FIG. 6b. The bone 25 is no longer depicted for reasons of simplicity. In this step a guide member 30 is placed onto the second portion 7 of the bone plate 2. The guide member 30 is attached by means of screw 35. At this stage auxiliary bone anchor means 18 may already be inserted in either the second portion 7 and/or the first longitudinal portion 6. FIG. 6c depicts the next step, where a blade guiding channel is reamed into the bone 25 with a chisel 42 which has the same shape and dimension as the blade 3. In order to guide the chisel 42, an additional chisel guiding member 33 may be placed on through hole 8. In the next step, which is shown in FIG. 6d, the blade 3 is inserted through the through hole 8 and into the blade guide channel. After full insertion of the blade 3 set screws 37 may be applied. Openings 9, 16 of the blade 3 are aligned with the bone anchor holes 5, 15. Bone anchors 4, 14 are then inserted into these bone anchor holes 5, 15 in the next step which is depicted in FIG. 6e. The bone anchor holes 5, 15 as well as the corresponding openings in guide member 30 are configured such that the bone anchors 4, 14 may only be inserted in a direction which leads them to advance through openings 9, 16 provided on blade 3. Further auxiliary bone anchors 18 may be inserted as needed. They may be used to tightly attach the bone plate 2 to the bone 25 or to fix further fragments of the bone 25. Preferably, when further fragments of the bone 25 are fixed by the auxiliary bone anchors 18, these are locked at various angles within auxiliary bone anchor holes 19, 24 by means of locking elements.

For example, a typical bone plate according to the present invention may have an overall length of 30-400 mm with a width of 5-70 mm. The blade thereby may have a length of 30-150 mm and be insertable at a fixed angle of between 30° and 60° relative to the underside of the plate. The bone anchors typically have a length of 10-100 mm with a diameter of 2.0-7.0 mm. However, a person skilled in the art will understand that any other dimensions may be used depending on the intended indication of the osteosynthesis system.

The invention claimed is:

1. A system for osteosynthesis of bone fractures comprising:
   at least one bone plate said bone plate having at least a first longitudinal plate portion, said first longitudinal plate portion including at least one through hole, and a second plate portion, said second plate portion including at least one bone anchor hole;
   at least one blade with a longitudinal axis; and
   at least one bone anchor,
   wherein said at least one blade further comprises at least one opening and is configured such as
   a) to be insertable at a predefined angle in relation to the bone plate through said through hole of the first longitudinal plate portion into a bone,
   b) wherein the at least one opening of the blade is configured such as to be aligned with said at least one bone anchor hole of the second plate portion when the blade is fully inserted into said through hole of the first longitudinal plate portion,
   c) such that the bone anchor may be inserted through said bone anchor hole of the second plate portion and extend through the blade,
   thus forming a truss-like structure between the bone plate, the bone anchor and the blade.

2. The system according to claim 1, wherein said blade further comprises connection means to reversibly connect said blade to said bone plate.

3. The system according to claim 1, wherein said blade comprises a first end and a second end and at least one fin element spanning the longitudinal axis from said first end to said second end, said at least one fin element preferably winding around said longitudinal axis in a spiral manner.

4. The system according to claim 3, wherein said at least one fin element winds around said longitudinal axis in a spiral manner for a turn of 90°.

5. The system according to claim 1, wherein said blade comprises one, two or more fin elements.

6. The system according to claim 5, wherein said fin elements are arranged at angles of 180°, 120° or 90° from one another.

7. The system according to claim 1, wherein said second portion of said bone plate and said blade comprise at least one additional bone anchor hole and at least one additional opening which are configured such as to be respectively aligned when the blade is fully inserted into said through hole.

8. The system according to claim 7, wherein the second portion and the blade additionally comprise at least one, two, three or four additional bone anchor holes and additional openings.

9. The system according to claim 1, wherein the second portion of the bone plate comprises at least one auxiliary bone anchor hole which is not aligned with an opening of the blade, allowing insertion of an auxiliary bone anchor under a variable angle in relation to the bone plate.

10. The system according to claim 9, wherein said at least one auxiliary bone anchor hole further comprises a locking element to lock a corresponding outer contour of an auxiliary bone anchor.

11. The system according to claim 10, wherein the locking element is in the form of a locking contour.

12. The system according to claim 1, wherein said second portion of the bone plate comprises a head section bulging out sideward of the bone plate.

13. The system according to claim 1, wherein said first longitudinal portion further comprises at least one auxiliary bone anchor hole.

14. The system according to claim 13, wherein said at least one auxiliary bone anchor hole includes a locking element to lock an auxiliary bone anchor in said hole.

15. The system according to claim 1, wherein said blade is configured such as to be at least one of self drilling and self cutting.

16. The system according to claim 1, wherein said osteosynthesis system comprises a set of blades with different predefined insertion angles.

17. A method for fracture fixation of a bone comprising the steps of:
- (a) Placing a bone plate on said fractured bone, wherein a first longitudinal portion is placed on a first bone fragment on one side of the fracture and a second portion is placed on a second bone fragment on the other side of the fracture;
- (b) inserting a blade at an angle in relation to the bone plate through a through hole of the first longitudinal plate portion into the bone, wherein said angle is selected such that the blade points in the direction of the second portion of the bone plate;
- (c) Inserting a bone anchor into the bone through at least one bone anchor hole of the second plate portion and through said at least one opening of the blade, thus forming a truss-like structure between the bone plate, the bone anchor and the blade.

18. The method according to claim 17, wherein prior to insertion of the blade, a blade insertion channel is formed.

19. The method according to claim 18, wherein said blade insertion channel is formed using a chisel.

\* \* \* \* \*